(12) United States Patent
Sugawara et al.

(10) Patent No.: US 8,034,962 B2
(45) Date of Patent: Oct. 11, 2011

(54) ACID ANHYDRIDE ESTER AND COMPOSITION THEREOF, AND HEAT-CURABLE RESIN COMPOSITION AND CURED PRODUCT THEREOF

(75) Inventors: Tomohiro Sugawara, Okayama (JP); Takeshi Koyama, Kanagawa (JP); Atsushi Okoshi, Okayama (JP); Takashi Sato, Kanagawa (JP); Shuichi Ueno, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 665 days.

(21) Appl. No.: 11/835,609

(22) Filed: Aug. 8, 2007

(65) Prior Publication Data
US 2008/0039591 A1 Feb. 14, 2008

(30) Foreign Application Priority Data

Aug. 9, 2006 (JP) ................. 2006-216937
Aug. 9, 2006 (JP) ................. 2006-216938

(51) Int. Cl.
*C07D 407/04* (2006.01)
*C08G 65/48* (2006.01)
(52) U.S. Cl. ..................... 549/244; 525/396
(58) Field of Classification Search ............. 525/396; 549/244
See application file for complete search history.

(56) References Cited

U.S. PATENT DOCUMENTS

| | | | | |
|---|---|---|---|---|
| 2,996,520 A | * | 8/1961 | Knobloch et al. | 549/244 |
| 3,063,969 A | * | 11/1962 | Stephens et al. | 526/271 |
| 3,140,299 A | * | 7/1964 | Loncrini | 549/244 |
| 3,238,184 A | * | 3/1966 | Stephens et al. | 528/361 |
| 3,477,976 A | * | 11/1969 | Shibazaki et al. | 525/443 |
| 3,711,514 A | * | 1/1973 | Quick | 549/244 |
| 3,833,618 A | * | 9/1974 | Piasek | 549/244 |
| 3,951,977 A | * | 4/1976 | Plasek et al. | 544/373 |

FOREIGN PATENT DOCUMENTS

| | | |
|---|---|---|
| EP | 1 506 952 A2 | 2/2005 |
| EP | 1 686 121 A1 | 8/2006 |
| EP | 1754734 A1 * | 2/2007 |
| JP | 61-188414 | 8/1986 |
| JP | 2001-114868 | 4/2001 |
| JP | 2002-097251 | 4/2002 |
| JP | 2003-026763 | 1/2003 |
| JP | 2005-036218 | 2/2005 |
| WO | WO 2005/049597 | 6/2005 |
| WO | WO 2005121202 A1 * | 12/2005 |
| WO | WO 2006129771 A1 * | 12/2006 |

OTHER PUBLICATIONS

Extended European Search Report dated Nov. 16, 2007, for Application No. EP 07 11 3853.

* cited by examiner

*Primary Examiner* — Mark Eashoo
*Assistant Examiner* — Megan McCulley
(74) *Attorney, Agent, or Firm* — Antonelli, Terry, Stout & Kraus, LLP.

(57) ABSTRACT

The present invention provides an acid anhydride ester obtained by esterifying cyclohexane-1,2,4-tricarboxylic acid-1,2-anhydride and a composition of the ester, and a heat-curable resin composition and a cured product of the composition. _Provided is an epoxy resin composition using the acid anhydride ester as a curing agent for an epoxy resin, the epoxy resin composition having, for example, the following properties (1), (2), and (3): (1) the epoxy resin composition has a low viscosity at room temperature, so the components of the composition can be favorably blended with each other, (2) the acid anhydride ester has a low vapor pressure at curing temperature, so no evaporation loss occurs after curing, and the intended design of blend is capable, and (3) a cured product to be made from the composition is colorless and transparent, and changes its color to a small extent even when the product is irradiated with light or heated for a long time period. The composition is suitably used as, for example, an encapsulant for a photoelectric conversion element such as a blue LED or a white LED, a molded article, a coating, or an adhesive.

6 Claims, No Drawings

ACID ANHYDRIDE ESTER AND COMPOSITION THEREOF, AND HEAT-CURABLE RESIN COMPOSITION AND CURED PRODUCT THEREOF

BACKGROUND OF THE INVENTION

1. Field of the Invention

The present invention relates to a novel acid anhydride ester and a composition of the ester, and a novel heat-curable resin composition and a cured product of the composition, and more specifically, to an acid anhydride ester and a composition of the ester, and a heat-curable resin composition and a cured product of the composition each of which is useful as: an encapsulant for a photoelectric conversion element typified by a light emitting diode such as a blue or white light emitting diode (hereinafter, abbreviated as "LED"); a raw material for a coating, adhesive, molded article, curing agent, polyimide resin, or the like; a modifier; a plasticizer; a lubricating oil raw material; an intermediate for a drug or agricultural chemical; a raw material for a coating; a toner resin; or the like.

2. Description of the Related Art

In recent years, blue LED's and white LED's each having high luminance have been developed, and have been finding use in an expanded variety of applications including bulletin boards, full-color displays, and backlights for portable phones. An acid anhydride curable epoxy resin has been conventionally used as an encapsulant for a photoelectric conversion element such as an LED because the resin is excellent in colorless and transparent nature. An alicyclic acid anhydride such as methyltetrahydrophthalic anhydride, hexahydrophthalic anhydride, or tetrahydrophthalic anhydride has been generally used as a curing agent for an epoxy resin for use in such photoelectric conversion element. Of those, methylhexahydrophthalic anhydride, methyltetrahydrophthalic anhydride, or the like which is a liquid at normal temperature has been mainly used because of its ease of handling.

However, when the above alicyclic acid anhydride is used as a curing agent, a curing accelerator must be added to the alicyclic acid anhydride in order that the alicyclic acid anhydride may be sufficiently cured because the alicyclic acid anhydride has low curing reactivity.

For example, triphenylphosphonium bromide (JP2000-344868 A), 2-ethyl-4-methylimidazole (JP 2001-114868 A), an ethyl hexanoate of 1,8-diazabicyclo[5.4.0]undecene-7 (JP2002-97251 A: Example 8), and tetraphenylphosphonium bromide (JP 2003-26763 A) have been used as curing accelerators each used in a curing agent made of an alicyclic acid anhydride.

An epoxy resin composition as an encapsulant for a photoelectric conversion element is exposed to the strong light emission energy of an LED at a high temperature for a long time period. Accordingly, the epoxy resin composition must show a colorless and transparent nature under heating for a long time period in order that the epoxy resin composition may find applications in blue LED's and white LED's. However, such curing accelerator as described above is not preferably used in an encapsulant for a photoelectric conversion element such as an LED because of the following reason: when the curing accelerator is used in a curing agent made of an alicyclic acid anhydride, the curing accelerator itself changes to a yellow color owing to heating for a long time period, with the result that the colorless and transparent nature of the encapsulant is impaired.

In addition, a conventional curing agent has a high vapor pressure, and part of the agent evaporates at the time of curing. Accordingly, the compounding ratio of the agent deviates from a target value, and it becomes difficult to obtain a cured product having target performance.

There has been proposed an epoxy resin composition using cyclohexane-1,2,4-tricarboxylic acid-1,2-anhydride as a curing agent (JP 2005-36218 A and WO 2005/49597). The composition has excellent curability without the use of any curing accelerator. A cured product of the composition is colorless and transparent, and changes its color to a small extent even when the cured product is irradiated with light having a high temperature and high energy. The composition can find applications in blue LED's and white LED's. However, the curing agent is a solid or a liquid having an extremely high viscosity at room temperature, so the ease with which the curing agent and any other component of the composition are blended with each other is problematic.

SUMMARY OF THE INVENTION

An object of the present invention is to provide an epoxy resin composition composed of an epoxy resin and a curing agent, the composition having, for example, the following properties (1), (2), and (3), and the composition being suitable as an encapsulant for a photoelectric conversion element such as a blue LED or a white LED:

(1) the epoxy resin composition has a low viscosity at room temperature, and the curing agent and a principal agent can be easily compounded with each other, (2) the curing agent has a low vapor pressure at curing temperature, so no evaporation loss occurs after curing, and the intended design of blend is capable, and (3) a product to be made from the composition is colorless and transparent, and changes its color to a small extent even when the product is irradiated with light or heated for a long time period.

The inventors of the present invention have made extensive studies with a view to solving the above-mentioned problems. As a result, the inventors have found that a novel acid anhydride ester obtained by esterifying cyclohexane-1,2,4-tricarboxylic acid-1,2-anhydride is adequate for the above object, and the acid anhydride ester and a composition of the ester each serve as a curing agent for an epoxy resin to be suitably used in, for example, an encapsulant for a photoelectric conversion element. Thus, the inventors have reached the present invention.

That is, the present invention relates to an acid anhydride ester and a composition of the ester, and a heat-curable resin composition and a cured product of the composition described below.

1. An acid anhydride ester represented by the following general formula (1):

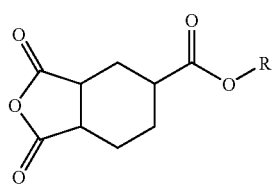

(1)

where R represents one of an alkyl group having 1 to 4 carbon atoms and a substituent represented by a formula (2), and $R^1$ in the formula (2) represents an alkylene group having 1 to 4 carbon atoms.

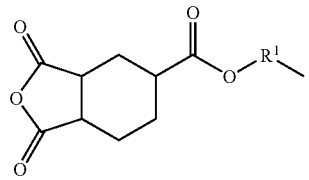

2. An acid anhydride ester according to Item 1, wherein R in the general formula (1) represents an alkyl group having 1 to 4 carbon atoms.

3. An acid anhydride ester according to Item 2, where R in the general formula (1) represents one of a methyl group, an ethyl group, a 1-propyl group, and a 2-propyl group.

4. A heat-curable resin composition including the acid anhydride ester according to any one of Items 1 to 3.

5. A heat-curable resin composition including: the acid anhydride ester according to any one of Items 1 to 3; and a compound having an epoxy ring.

6. A cured product obtained by curing the heat-curable resin composition according to Item 5.

7. An acid anhydride ester composition including: (A) the acid anhydride ester according to any one of Items 1 to 3; and (B) cyclohexane-1,2,4-tricarboxylic acid-1,2-anhydride.

8. An acid anhydride ester composition according to Item 7, where a weight ratio (A):(B) is 95 to 5:5 to 95.

9. An acid anhydride ester composition according to Item 8, where a weight ratio (A):(B) is 60 to 40:10 to 90.

10. A curing agent including the acid anhydride ester composition according to any one of Items 7 to 9.

11. A heat-curable resin composition including: the acid anhydride ester composition according to any one of Items 7 to 9; and a compound having an epoxy ring.

12. A cured product obtained by curing the heat-curable resin composition according to Item 11.

According to the present invention, there can be provided an epoxy resin composition using the above acid anhydride ester as a curing agent for an epoxy resin, the epoxy resin composition having, for example, the following properties (1), (2), and (3), and the epoxy resin composition being suitably used as, for example, an encapsulant for a photoelectric conversion element such as a blue LED or a white LED, a molded article, a coating, or an adhesive:

(1) the epoxy resin composition has a low viscosity at room temperature, so the components of the composition can be favorably blended with each other,
(2) the acid anhydride ester has a low vapor pressure at curing temperature, so no evaporation loss occurs after curing, and the intended design of blend is capable, and
(3) a cured product to be made from the composition is colorless and transparent, and changes its color to a small extent even when the product is irradiated with light or heated for a long time period.

In particular, an acid anhydride ester composition containing (B) cyclohexane-1,2,4-tricarboxylic acid-1,2-anhydride cures without the addition of any curing accelerator, and a cured product excellent in, for example, thermal shock resistance can be obtained.

DETAILED DESCRIPTION OF THE INVENTION

An acid anhydride ester of the present invention is an acid anhydride ester represented by the general formula (1). R in the general formula (1) represents an alkyl group having 1 to 4 carbon atoms, or a substituent represented by the formula (2), and $R^1$ in the formula (2) represents an alkylene group having 1 to 4 carbon atoms.

R in the general formula (1) preferably represents an alkyl group having 1 to 4 carbon atoms, or more preferably represents a methyl group, an ethyl group, a 1-propyl group, or a 2-propyl group.

The acid anhydride ester represented by the general formula (1) can be synthesized by: causing, for example, cyclohexane-1,2,4-tricarboxylic acid-1,2-anhydride and an alcohol or a glycol to react with each other to provide an esterified product; and subjecting the esterified product to a rearrangement reaction under heating while drawing produced water. At the time of the reaction, the removal of produced water can be facilitated by (i) charging an azeotropic agent for water, (ii) performing the reaction while circulating an inert gas, or (iii) performing the reaction while reducing a pressure. Two or more of those methods (i) to (iii) can be employed in combination. In addition, the reaction may be performed without the use of any catalyst or by using an acid catalyst.

Examples of the alcohol to be used in the reaction include methanol, ethanol, propanol, and butanol. In addition, examples of the glycol include ethylene glycol and butylene glycol. Each of those alcohols may be used alone, or two or more kinds of the alcohols may be used as a mixture.

An acid anhydride ester in which R in the general formula (1) represents an alkyl group having 1 to 4 carbon atoms, that is, a cyclohexane-1,2,4-tricarboxylic acid-1,2-anhydride-4-alkyl ester can be produced by the following method using, for example, at least one of solid 1,2,4-cyclohexanetricarboxylic acid-1,2-anhydride and liquid 1,2,4-cyclohexanetricarboxylic acid-1,2-anhydride, or solid 1,2,4-cyclohexanetricarboxylic acid as a raw material.

(a) The ester is produced by such method as described above including the steps of: adding a monohydric alcohol to cyclohexane-1,2,4-tricarboxylic acid-1,2-anhydride; and subjecting the resultant to a rearrangement reaction under heating while drawing produced water. The alcohol of which the ester is constituted is added to cyclohexane-1,2,4-tricarboxylic acid-1,2-anhydride, and the whole is heated, whereby the rearrangement reaction, and reaction for forming an anhydride, of a carboxyester group including an alkyl group of the added alcohol occur. Thus, the cyclohexane-1,2,4-tricarboxylic acid-1,2-anhydride-4-alkyl ester is obtained.

(b) The carboxyl group of cyclohexane-1,2,4-tricarboxylic acid-1,2-anhydride is turned into an acid chloride, and the site is caused to react with the corresponding alcohol, whereby the cyclohexane-1,2,4-tricarboxylic acid-1,2-anhydride-4-alkyl ester is produced.

(c) Cyclohexane-1,2,4-tricarboxylic acid as a raw material for cyclohexane-1,2,4-tricarboxylic acid-1,2-anhydride and a monohydric alcohol are caused to react with each other. That is, the ester is produced by a method including the steps of: adding the monohydric alcohol to cyclohexane-1,2,4-tricarboxylic acid; and subjecting the resultant to a rearrangement reaction under heating while drawing produced water. At the time of the reaction, as in the case of the method (a), the removal of produced water can be facilitated by (i) charging an azeotropic agent for water, (ii) performing the reaction while circulating an inert gas, or (iii) performing the reaction while reducing a pressure. Two or more of those methods (i) to (iii) can be employed in combination. The reaction may be performed without the use of any catalyst or by using an acid catalyst. In the method (c), the alcohol of which the ester is constituted is added to cyclohexane-1,2,4-tricarboxylic acid, and the whole is heated, whereby the rearrangement reaction, and reaction for forming an anhydride, of a carboxyester group including an alkyl group of the added alcohol occur. Thus, the cyclohexane-1,2,4-tricarboxylic acid-1,2-anhydride-4-alkyl ester is obtained.

In any one of the methods (a) to (c), a reaction is performed at a temperature of 180° C. to 300° C., or preferably 190° C. to 280° C. because the reaction proceeds at a low rate at low temperatures, and a secondary reaction such as a decarboxylation reaction is apt to proceed at high temperatures. The reaction is preferably performed under normal pressure or reduced pressure. When the reaction is performed under reduced pressure, the pressure is preferably 500 Torr (65 kPa) or less, or more preferably 200 Torr (26 kPa) or less. The reaction is performed for a time period of preferably 24 hours or shorter, or more preferably 1 to 16 hours in terms of production efficiency, though the time period varies depending on a temperature. The compounding ratio of a raw material is not particularly limited; a ratio of the alcohol to cyclohexane-1,2,4-tricarboxylic acid or an anhydride of the acid is in the range of preferably 0.1 to 3.0, or more preferably 0.1 to 1.0. Either a batch type method or a continuous type method may be adopted for the reaction.

Upon production of the acid anhydride ester of the present invention, a liquid acid anhydride ester showing an additionally good color value and having a low viscosity at normal temperature can be obtained by providing a step of purifying the acid anhydride ester by distillation at the time when a coarse product of the acid anhydride ester is obtained. In this case, the color value (Hazen) of the acid anhydride ester is 100 or less, or preferably 50 or less.

Distillation may be of a batch type or a continuous type; a method showing a small heat history is preferable in order that the decomposition of a target product and the production of a high-boiling-point fraction may be suppressed. In addition, distillation is preferably performed in stages in order that the target product may be favorably separated from a by-product.

Distillation is performed under a pressure of preferably 15 mmHg (2 kPa) or less, or more preferably 10 mmHg (1.3 kPa) or less. Such pressure can suppress the decomposition of the target product and the production of a high-boiling-point component.

The acid anhydride ester of the present invention can be used as a curing agent for, for example, an epoxy group-containing resin. An acid anhydride ester composition containing the acid anhydride ester and cyclohexane-1,2,4-tricarboxylic acid-1,2-anhydride can also be used as a curing agent. Each of those curing agents can be mixed with any one of various acid anhydrides such as phthalic anhydride subjected to nucleus hydrogenation and methylphthalic anhydride subjected to nucleus hydrogenation as required.

When the acid anhydride ester composition of the present invention is composed of (A) an acid anhydride ester represented by the general formula (1), in particular, a cyclohexane-1,2,4-tricarboxylic acid-1,2-anhydride-4-alkyl ester and (B) cyclohexane-1,2,4-tricarboxylic acid-1,2-anhydride, a weight ratio (A):(B) is preferably 95 to 5:5 to 95, or more preferably 60 to 10:40 to 90. The range varies depending on an alkyl group of the acid anhydride ester. However, the curability of the epoxy group-containing resin is improved by adding the component (A) with the component (B) at a ratio in the range, so a cured product excellent in, for example, transparency (light transmittance) can be easily obtained without the use of any curing accelerator.

A heat-curable resin composition of the present invention is a heat-curable resin composition (I) containing an acid anhydride ester and a compound having an epoxy ring, or a heat-curable resin composition (II) containing an anhydride ester composition and a compound having an epoxy ring.

The compound having an epoxy ring to be used in the present invention is an organic or inorganic compound having an ethylene oxide skeleton in any one of its molecules. Examples of an organic compound having an epoxy ring include: a bisphenol A type epoxy resin; a bisphenol F type epoxy resin; a cresol novolac type epoxy resin; a phenol novolac type epoxy resin; a biphenyl type epoxy resin; a stilbene type epoxy resin; a hydroquinone type epoxy resin; a naphthalene skeleton type epoxy resin; a tetraphenylolethane type epoxy resin; a DPP type epoxy resin; a trishydroxyphenylmethane type epoxy resin; a dicyclopentadiene phenol type epoxy resin; an alicyclic epoxy resin such as 3,4-epoxycyclohexylmethyl-3',4'-epoxycyclohexane carboxylate or vinylcyclohexene diepoxide; a polyglycidyl ester of a polybasic acid such as diglycidyl ether of bisphenol A added with ethylene oxide, diglycidyl ether of bisphenol A added with propylene oxide, cyclohexane dimethanol diglycidyl ether, a polyglycidyl ether of an aliphatic polyhydric alcohol, or diglycidyl ester of hexahydrophthalic anhydride; an alkyl glycidyl ether such as butyl glycidyl ether or lauryl glycidyl ether; and a glycidyl ether having one epoxy group such as phenyl glycidyl ether or cresyl glycidyl ether. The examples further include products obtained by subjecting the above epoxy resins to nucleus hydrogenation (epoxy resins subjected to nucleus hydrogenation). In addition, examples of an inorganic compound having an epoxy ring include compounds each containing an epoxy ring in silicone skeleton thereof. Each of those resins can be used alone, or two or more kinds of them can be appropriately mixed before use.

An epoxy resin subjected to nucleus hydrogenation made of, in particular, 3,4-epoxycyclohexylmethyl-3',4'-epoxycyclohexane carboxylate, a polyglycidyl ester of a polybasic acid such as cyclohexane dimethanol diglycidyl ether or diglycidyl ester of hexahydrophthalic anhydride, or the like out of those compounds each having an epoxy ring is more preferably used because the resin improves the colorless and transparent nature of the heat-curable resin composition.

The loadings of the compound having an epoxy ring and one of the acid anhydride ester and the acid anhydride ester composition (which may be referred to as curing agents) in the heat-curable resin composition of the present invention are not particularly limited as long as a predetermined effect can be obtained; in ordinary cases, a curing agent amount (in the case of the acid anhydride ester composition, the total number of moles of the composition) is 0.1 to 2 moles, preferably 0.2 to 1.0 mole, or more preferably 0.3 to 1.0 mole with respect to one equivalent of an epoxy group (that is, the average molecular weight of groups each having one epoxy ring). A curing agent amount of 0.1 mole or more accelerates the progress of the curing of the heat-curable resin composition. A curing agent amount of 2 moles or less does not cause a reduction in glass transition temperature (Tg) or hygroscopicity of a cured product of the heat-curable resin composition, so the colorless and transparent nature of the product is not impaired, and the product does not change its color under heating for a long time period.

A curing accelerator can be appropriately used in the heat-curable resin composition (I) of the present invention composed of an epoxy group-containing resin and the acid anhydride ester to such an extent that an effect of the present invention is not impaired. In addition, the heat-curable resin composition (II) of the present invention composed of an epoxy group-containing resin and the acid anhydride ester composition does not necessarily require a curing accelerator.

A curing accelerator can be appropriately used in the heat-curable resin composition (II) to such an extent that the effect of the present invention is not impaired, though the use of the curing accelerator in an encapsulant for a photoelectric conversion element such as an LED is not preferable because the use is apt to impair the colorless and transparent nature of the encapsulant.

Examples of the curing accelerator in each of the heat-curable resin compositions (I) and (II) include: tertiary amines such as benzyldimethylamine, tris(dimethylaminomethyl)phenol, and dimethylcyclohexylamine; imidazoles such as 1-cyanoethyl-2-ethyl-4-methylimidazole, 2-ethyl-4-methylimidazole, and 1-benzyl-2-methylimidazole; organophosphorus compounds such as triphenylphosphine and triphenyl phosphite; quaternary phosphonium salts such as tetraphenylphosphonium bromide and tetra-n-butylphosphonium bromide; diazabicycloalkenes such as 1,8-diazabicyclo[5.4.0]undecene-7 and the like, and organic salts of 1,8-diazabicyclo[5.4.0]undecene-7 and the like; organometallic compounds such as zinc octylate, tin octylate, and an aluminum acetylacetone complex; quaternary ammonium salts such as tetraethylammonium bromide and tetrabutylammonium bromide; boron compounds such as boron trifluoride and triphenyl borate; and metal halides such as zinc chloride and stannic chloride. Further, a potential curing accelerator typified by: a high-melting-point dispersion type potential accelerator such as a high-melting-point imidazole compound, dicyandiamide, or an amine-added accelerator obtained by adding an amine to an epoxy resin or the like; a microcapsule type potential accelerator obtained by coating the surface of an imidazole-, phosphorus-, or phosphine-based accelerator with a polymer; an amine salt type potential curing accelerator; a high temperature dissociation type, heat cationic polymerization type potential curing accelerator such as a Lewis acid salt or a Bronsted acid salt; or the like canal so be used. Each of those curing accelerators can be used alone, or two or more kinds of them can be used as a mixture.

The loading of a curing accelerator when the curing accelerator is used in each of the heat-curable resin composition (I) and the heat-curable resin composition (II) is not particularly limited as long as a predetermined effect can be obtained; in ordinary cases, a curing accelerator content is 0.001 to 2 weight %, or preferably 0.01 to 1.0 weight % with respect to the weight of the heat-curable resin composition. A curing accelerator content of 0.001 weight % or more accelerates the curing of the composition. A curing accelerator content of 2 weight % or less neither impairs the colorless and transparent nature of a cured product of the composition nor largely changes the color of the product under heating for a long time period.

The heat-curable resin composition of the present invention (the following description is common to the heat-curable resin compositions (I) and (II)) can be blended with any one of additives such as: aliphatic polyols such as ethylene glycol and propylene glycol; carbon dioxide gas generation inhibitors such as an aliphatic or aromatic carboxylic acid compound, and a phenol compound; flexibility imparting agents such as polyalkylene glycol; oxidation inhibitors; plasticizers; lubricants; coupling agents such as a silane coupling agent; surface treatment agents for inorganic fillers; flame retardants; antistatic agents; colorants; leveling agents; ion trapping agents; sliding property improvers; impact resistance improvers such as various rubbers and organic polymer beads; thixotropy imparting agents; surfactants; surface tension depressants; defoaming agents; anti-settling agents; light diffusing agents; UV absorbers; antioxidants; release agents; fluorescent agents; and conductive fillers as required to such an extent that the properties of the curing agent to be obtained are not impaired.

A method of curing the heat-curable resin composition of the present invention is not particularly limited, and a conventionally known curing device such as a closed curing oven or a tunnel oven capable of continuously curing the composition can be adopted. A heating source is not particularly limited, and the composition can be heated by a conventionally known method such as the circulation of hot air, infrared heating, or high frequency heating. The composition is preferably cured at a temperature of 80 to 250° C. for a time period of 30 seconds to 10 hours. When one wishes to reduce the internal stress of a cured product to be obtained, the following procedure is preferably adopted: the composition is precured at 80 to 120° C. for 0.5 to 5 hours before the composition is postcured at 120 to 180° C. for 0.1 to 5 hours. When one aims to cure the composition in a short time period, the composition is preferably cured at 150 to 250° C. for 30 seconds to 30 minutes.

Each of the acid anhydride ester and acid anhydride ester composition of the present invention can be used mainly as a curing agent for a heat-curable resin composition that can be suitably used in, for example, a coating liquid for the protective film of a color filter of which a liquid crystal display device (LCD), a solid state imaging device (CCD), an electroluminescence (EL) device, or the like is constituted.

In addition, each of the acid anhydride ester and acid anhydride ester composition of the present invention can find use in other applications where a laminated plate or insulating property is not necessarily needed including: curing agents for heat-curable resin compositions for use in various FRP molded articles, various coating materials, adhesives, decorative materials, and the like; raw materials for polyimide resins, polyamideimide resins, polyester resins, alkyd resins, and the like; modifiers; plasticizers; lubricating oil raw materials; intermediates for drugs and agricultural chemicals; resin raw materials for coatings; and resins for toner.

The heat-curable resin composition of the present invention can be used as, for example, an encapsulant for a blue LED or a white LED because a cured product of the composition is colorless and transparent, and changes its color to a small extent even under heating for a long time period.

However, the applications of the heat-curable resin composition of the present invention are not limited to those described above, and the composition can find use in other applications where transparency is requested including: insulative encapsulants for photoelectric conversion elements typified by light emitting elements and photoconductive elements such as an LED and semiconductor laser, light receiving elements such as a photodiode, a solar cell, a phototransistor, and a photothyristor, and optically coupled devices such as a photocoupler and a photointerrupter; adhesives for liquid crystal and the like; resins for stereo lithography; surface coating agents for plastics, glass, metals, and the like; and decorative materials.

Further, the heat-curable resin composition of the present invention is applicable to, for example, an insulative encapsulant or molded article having a thickness of 2 mm or more by a conventionally known method such as potting, casting, filament winding, or lamination. Specific examples of applications where the composition can be used include: insulative encapsulants for heavy electric devices such as a mold potential transformer, a mold transformer (a current transformer (CT), a zero layer current transformer (ZCT), a potential transformer (PT), or an installation type potential transformer (ZPT)), a gas opening and closing part (insulating spacer, supporting glass, operating rod, closed terminal, bushing, insulating column, or the like), a solid isolating switch part, an overhead distribution line automatic control device part (rotating glass, voltage detecting element, overall capacitor, or the like), an underground distribution line device part (mold discone, power transformer, or the like), a power capacitor, resin glass, and a coil for a linear motor car; and impregnating varnish for coils for various rotating devices (such as generator and motor). In addition, the composition can find use in applications including: potting resins for flyback transformers, ignition coils, AC capacitors, and the like; transparent sealing resins for LED's, detectors, emitters, photocouplers, and the like; and insulative sealing resins for use in the field of weak electricity such as impregnating resins for film capacitors and various coils.

Hereinafter, the present invention will be described in detail by way of examples and comparative examples. However, the present invention should not be construed as being limited to the following examples.

It should be noted that composition analysis and the evaluation of a cured product were performed as described below in, for example, any one of the following examples.

A. Composition Analysis

A product was analyzed and identified by NMR and GC-MS. Measurement conditions are as shown below.

(1) NMR analysis
Device: JNM-AL 400 manufactured by JEOL Ltd.
Solvent: Heavy chloroform (2) GC-MS analysis
Device: GCMS-QP 1100EX manufactured by Shimadzu Corporation
Column: HR-1 manufactured by Shinwa Chemical Industries, Ltd. (0.32 φm×25 m)

B. Evaluation of Cured Product

A resin composition obtained in each of examples and comparative examples was introduced into a mold measuring 5 cm by 5 cm so as to have a thickness of 3 mm, and was precured by heating in an open system with a hot air dryer. After that, the composition was postcured by additional heating in order that the composition might be completely cured. The composition was heated at 120° C. for 3 hours in the precuring while the composition was heated at 150° C. for 2 hours in the postcuring.

(1) The transmittance of the resultant composition for a light beam having a wavelength of 400 nm was measured by the following method at each of the following three time points (i), (ii), and (iii): (i) an initial stage, (ii) a time point after a 150° C. heat resistance test, and (iii) a time point after a UV resistance test. In addition, the cured product was subjected to (2) the following thermal shock resistance test, and, further, (3) the percentage by which the weight of the composition reduced in each of the precuring and the postcuring was measured.

(Method of Measuring Transmittance for Light Beam having Wavelength of 400 nm)

The transmittance of a cured product having a thickness of about 3 mm for a light beam having a wavelength of 400 nm was measured with a recording spectrophotometer (UV-3100 PC manufactured by Shimadzu Corporation), and the measured value was converted into a light beam transmittance of a thickness of 1 mm (%/mm).

(150° C. Heat Resistance Test)

A cured product was exposed in a gear oven at 150° C. for 120 hours, and the transmittance of the cured product for a light beam having a wavelength of 400 nm was measured.

(UV Resistance Test)

A cured product was irradiated with UV light having a wavelength of 300 to 400 nm from an EYE Super UV Tester (SUV-W11 manufactured by IWASAKI ELECTRIC CO., LTD.) at a dose of 68 mw/cm$^2$. 120 hours after the irradiation, the transmittance of the cured product for a light beam having a wavelength of 400 nm was measured.

(Thermal Shock Resistance Test)

A cured product containing a copper piece was repeatedly subjected to a heat cycle "−40° C./30 minutes→25° C./5 minutes→100° C./30 minutes→25° C./5 minutes" 100 times. The cured product was evaluated as "x" when a crack was generated while the cured product was evaluated as "o" when no crack was generated.

Example 1

100 g of solid cyclohexane-1,2,4-tricarboxylic acid-1,2-anhydride (manufactured by MITSUBISHI GAS CHEMICAL COMPANY, INC.) were loaded into a four-necked flask provided with a sleeve pipe and a cooling pipe, and were heated to 180° C. 10.65 g of ethanol were dropped to the anhydride from a dropping funnel over 1 hour. The mixture was stirred at 180° C. for 1 hour, and then 10 ml of orthoxylene were added as an azeotropic agent to the mixture, and the whole was refluxed while being stirred. The resultant was heated at 235° C. for 11 hours while produced water was drawn. As a result, a theoretical amount of water was drawn. The resultant reaction liquid was distilled under reduced pressure in stages corresponding to a number of theoretical stages of 10, and a main product was isolated under a pressure of 7 mmHg (1.0 kPa) at 200° C.

A molecular ion peak and a fragment peak in NMR analysis and GC-MS analysis shown in Tables 1 and 2 showed that the above main product was cyclohexane-1,2,4-tricarboxylic acid-1,2-anhydride-4-ethyl ester, and that the cyclohexane-1,2,4-tricarboxylic acid-1,2-anhydride-4-ethyl ester were the mixture of two kinds of stereoisomers shown in the following formulae (3) and (4).

In addition, the composition of the main product was analyzed by a method based on internal standard analysis. As a result, the main product contained cyclohexane-1,2,4-tricarboxylic acid-1,2-anhydride-4-ethyl ester at a purity of 96.5 weight %, and contained cyclohexane-1,2,4-tricarboxylic acid-1,2-anhydride as a raw material, a diester compound, and a triester compound at contents of 2 weight %, 1 weight %, and 0.4 weight %, respectively. Cyclohexane-1,2,4-tricarboxylic acid-1,2-anhydride-4-ethyl ester was a liquid, and had a viscosity of 0.65 Pa·s at 25° C.

TABLE 1

$^1$H-NMR

| Chemical shift | Signal shape | H number |
|---|---|---|
| 1.24-1.29 | multiplet | 9 |
| 1.62-1.67 | multiplet | 8 |
| 1.95-2.45 | multiplet | 16 |
| 3.12-3.13 | multiplet | 3 |
| 3.14-3.16 | multiplet | 1 |
| 3.41-3.43 | multiplet | 2 |
| 4.11-4.19 | multiplet | 6 |
| Ref. signal | 7.24 ppm Heavy chloroform signal | |

TABLE 2

13C-NMR

| Chemical shift | Signal shape | C number |
|---|---|---|
| 13.99 | singlet | 1 |
| 14.04 | singlet | 1 |
| 20.61 | singlet | 1 |
| 23.27 | singlet | 1 |
| 23.85 | singlet | 1 |
| 24.50 | singlet | 1 |
| 24.62 | singlet | 1 |
| 27.27 | singlet | 1 |
| 37.82 | singlet | 1 |
| 38.95 | singlet | 1 |
| 39.43 | singlet | 1 |
| 39.48 | singlet | 1 |
| 39.62 | singlet | 1 |
| 39.69 | singlet | 1 |
| 60.78 | singlet | 1 |
| 60.86 | singlet | 1 |
| 17.87 | singlet | 1 |
| 172.26 | singlet | 1 |
| 172.35 | singlet | 1 |
| 172.43 | singlet | 1 |
| 173.49 | singlet | 1 |
| 173.60 | singlet | 1 |
| Ref. signal | 77.0 ppm Heavy chloroform signal | |

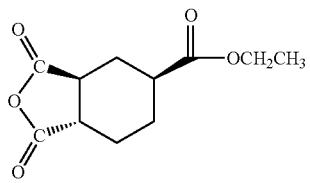

(3)

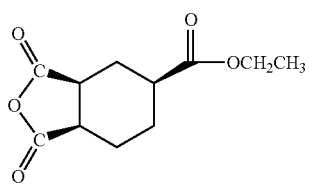

(4)

Example 2

100 g of solid cyclohexane-1,2,4-tricarboxylic acid-1,2-anhydride (manufactured by MITSUBISHI GAS CHEMICAL COMPANY, INC.) were loaded into a four-necked flask provided with a sleeve pipe and a cooling pipe, and were heated to 180° C. 7.41 g of methanol were dropped to the anhydride from a dropping funnel over 1 hour. The mixture was stirred at 180° C. for 1 hour, and then 10 ml of orthoxylene were added as an azeotropic agent to the mixture, and the whole was refluxed while being stirred. The resultant was heated at 235° C. for 11 hours while produced water was drawn. As a result, a theoretical amount of water was drawn. The resultant reaction liquid was distilled under reduced pressure in stages corresponding to a number of theoretical stages of 10, and a main product was isolated under a pressure of 5 mmHg (0.7 kPa) at 185° C.

A molecular ion peak and a fragment peak in NMR analysis and GC-MS analysis shown in Tables 3 and 4 showed that the above main product was cyclohexane-1,2,4-tricarboxylic acid-1,2-anhydride-4-methyl ester, and that the molecules of cyclohexane-1,2,4-tricarboxylic acid-1,2-anhydride-4-methyl ester were the mixture of the molecules of two kinds of stereoisomers shown in the following formulae (5) and (6).

In addition, the composition of the main product was analyzed by a method based on internal standard analysis. As a result, the main product contained cyclohexane-1,2,4-tricarboxylic acid-1,2-anhydride-4-methyl ester at a purity of 99 weight %, and contained cyclohexane-1,2,4-tricarboxylic acid-1,2-anhydride, a diester compound, and a triester compound as raw materials at contents of 0.1 weight %, 1 weight %, and 0.1 weight %, respectively. Cyclohexane-1,2,4-tricarboxylic acid-1,2-anhydride-4-methyl ester was a liquid, and had a viscosity of 1.42 Pa·s at 25° C.

TABLE 3

1H-NMR

| Chemical shift | Signal shape | H number |
|---|---|---|
| 1.59-1.67 | multiplet | 3.7 |
| 1.93-2.04 | multiplet | 2.6 |
| 2.15-2.17 | multiplet | 1 |
| 2.26-2.48 | multiplet | 3.6 |
| 3.12-3.18 | multiplet | 1.5 |
| 3.25-3.35 | multiplet | 0.5 |
| 3.42-3.47 | multiplet | 1 |
| 3.69-3.72 | multiplet | 4.6 |
| Ref. signal | 7.24 ppm Heavy chloroform signal | |

TABLE 4

13C-NMR

| Chemical shift | Signal shape | C number |
|---|---|---|
| 20.70 | singlet | 1 |
| 23.47 | singlet | 1 |
| 23.95 | singlet | 1 |
| 24.63 | singlet | 1 |
| 24.76 | singlet | 1 |
| 27.37 | singlet | 1 |
| 37.88 | singlet | 1 |
| 38.89 | singlet | 1 |
| 39.56 | singlet | 1 |
| 39.69 | singlet | 1 |
| 39.76 | singlet | 1 |
| 52.10 | singlet | 1 |
| 52.14 | singlet | 1 |
| 127.15 | singlet | 1 |
| 140.99 | singlet | 1 |
| 172.06 | singlet | 1 |
| 172.43 | singlet | 1 |
| 172.55 | singlet | 1 |
| 172.60 | singlet | 1 |
| 174.13 | singlet | 1 |
| 174.20 | singlet | 1 |
| Ref. signal | 77.0 ppm Heavy chloroform signal | |

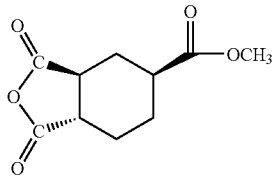

(5)

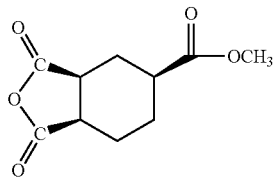

(6)

Example 3

100 g of solid cyclohexane-1,2,4-tricarboxylic acid-1,2-anhydride (manufactured by MITSUBISHI GAS CHEMICAL COMPANY, INC.) were loaded into a four-necked flask provided with a sleeve pipe and a cooling pipe, and were heated to 180° C. 13.89 g of 1-propanol were dropped to the anhydride from a dropping funnel over 1 hour. The mixture was stirred at 180° C. for 1 hour, and then 10 ml of orthoxylene were added as an azeotropic agent to the mixture, and the whole was refluxed while being stirred. The resultant was heated at 235° C. for 11 hours while produced water was drawn. As a result, a theoretical amount of water was drawn. The resultant reaction liquid was distilled under reduced pressure in stages corresponding to a number of theoretical stages of 10, and a main product was isolated under a pressure of 8 mmHg (1.0 kPa) at 203° C.

A molecular ion peak and a fragment peak in NMR analysis and GC-MS analysis shown in Tables 5 and 6 showed that the above main product was cyclohexane-1,2,4-tricarboxylic acid-1,2-anhydride-4-(1-propyl) ester, and that the molecules of cyclohexane-1,2,4-tricarboxylic acid-1,2-anhydride-4-(1-propyl) ester were the mixture of the molecules of two kinds of stereoisomers shown in the following formulae (7) and (8).

In addition, the composition of the main product was analyzed by a method based on internal standard analysis. As a result, the main product contained cyclohexane-1,2,4-tricarboxylic acid-1,2-anhydride-4-(1-propyl) ester at a purity of 97 weight %, and contained cyclohexane-1,2,4-tricarboxylic acid-1,2-anhydride, a diester compound, and a triester compound as raw materials at contents of 0.1 weight %, 2 weight %, and 0.1 weight %, respectively. Cyclohexane-1,2,4-tricarboxylic acid-1,2-anhydride-4-(1-propyl) ester was a liquid, and had a viscosity of 0.47 Pa·s at 25° C.

TABLE 5

| $^1$H-NMR | | |
|---|---|---|
| Chemical shift | Signal shape | H number |
| 0.92-0.97 | multiplet | 5 |
| 1.59-1.70 | multiplet | 7.4 |
| 1.95-2.04 | multiplet | 7.3 |
| 2.14-2.47 | multiplet | 7.6 |
| 3.13-3.17 | multiplet | 1.6 |
| 3.25-3.35 | multiplet | 0.6 |
| 3.41-3.45 | multiplet | 1 |
| 4.02-4.08 | multiplet | 3.3 |
| Ref. signal | 7.24 ppm Heavy chloroform signal | |

TABLE 6

| $^{13}$C-NMR | | |
|---|---|---|
| Chemical shift | Signal shape | C number |
| 10.36 | singlet | 1 |
| 10.39 | singlet | 1 |
| 20.75 | singlet | 1 |
| 21.90 | singlet | 1 |
| 21.94 | singlet | 1 |
| 23.50 | singlet | 1 |
| 23.97 | singlet | 1 |
| 24.71 | singlet | 1 |
| 24.83 | singlet | 1 |
| 27.48 | singlet | 1 |
| 38.04 | singlet | 1 |
| 39.14 | singlet | 1 |
| 39.58 | singlet | 1 |
| 39.62 | singlet | 1 |
| 39.75 | singlet | 1 |
| 39.82 | singlet | 1 |
| 66.50 | singlet | 1 |
| 66.56 | singlet | 1 |
| 172.11 | singlet | 1 |
| 172.49 | singlet | 1 |
| 172.61 | singlet | 1 |
| 172.66 | singlet | 1 |
| 173.74 | singlet | 1 |
| 173.83 | singlet | 1 |
| Ref. signal | 77.0 ppm Heavy chloroform signal | |

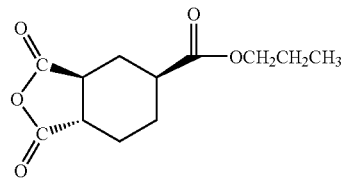

(7)

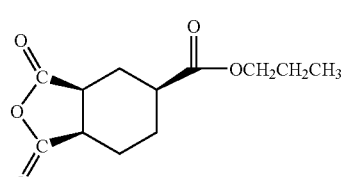

(8)

Example 4

81 parts by weight of cyclohexane-1,2,4-tricarboxylic acid-1,2-anhydride-4-ethyl ester obtained in Example 1, 50 parts by weight of an alicyclic epoxy resin (Celoxide manufactured by DAICEL CHEMICAL INDUSTRIES, LTD., epoxy equivalent 126), and 0.13 part by weight of benzyldimethylamine were mixed, whereby a heat-curable resin composition was obtained. The resin composition had a viscosity of 0.28 Pa·s at 30° C.

Table 7 shows the percentage by which the weight of the resultant resin composition reduces in each of the precuring and the postcuring, and the results of the evaluation of the cured product.

It should be noted that, in Table 7, the term "acid anhydride" refers to cyclohexane-1,2,4-tricarboxylic acid-1,2-anhydride, and the term "acid anhydride ester" refers to an ester of the acid anhydride. In addition, a numerical value in the parentheses of each of the acid anhydride ester and the acid anhydride in the column "Composition" represents the content (weight %) of each of the acid anhydride ester and the acid anhydride in a composition composed of both of them.

Example 5

76 parts by weight of cyclohexane-1,2,4-tricarboxylic acid-1,2-anhydride-4-methyl ester obtained in Example 2, 50 parts by weight of an alicyclic epoxy resin (Celoxide manufactured by DAICEL CHEMICAL INDUSTRIES, LTD., epoxy equivalent 126), and 0.13 part by weight of benzyldimethylamine were mixed, whereby a heat-curable resin composition was obtained. The resin composition had a viscosity of 0.42 Pa·s at 30° C.

Table 7 shows the percentage by which the weight of the resultant resin composition reduces in each of the precuring and the postcuring, and the results of the evaluation of the cured product.

Example 6

86 parts by weight of cyclohexane-1,2,4-tricarboxylic acid-1,2-anhydride-4-(1-propyl) ester obtained in Example 3, 50 parts by weight of an alicyclic epoxy resin [Celoxide manufactured by DAICEL CHEMICAL INDUSTRIES, LTD., epoxy equivalent 126], and 0.13 part by weight of benzyldimethylamine were mixed, whereby a heat-curable resin composition was obtained. The resin composition had a viscosity of 0.30 Pa·s at 30° C.

Table 7 shows the percentage by which the weight of the resultant resin composition reduces in each of the precuring and the postcuring, and the results of the evaluation of the cured product.

Example 7

76 parts by weight (0.36 mol) of an acid anhydride ester composition composed of 50 weight % of cyclohexane-1,2,4-tricarboxylic acid-1,2-anhydride and 50 weight % of cyclohexane-1,2,4-tricarboxylic acid-1,2-anhydride-4-ethyl ester (having an average molecular weight of 212.2) obtained in Example 1 and 50 parts by weight of an alicyclic epoxy resin [Celoxide manufactured by DAICEL CHEMICAL INDUSTRIES, LTD., epoxy equivalent 126] were mixed (acid anhydride mol/epoxy equivalent ratio 0.9), whereby a heat-curable resin composition was obtained. The resin composition had a viscosity of 1.3 Pa·s at 30° C.

Table 7 shows the percentage by which the weight of the resultant resin composition reduces in each of the precuring and the postcuring, and the results of the evaluation of the cured product.

Example 8

72 parts by weight (0.36 mol) of an acid anhydride ester composition composed of 90 weight % of cyclohexane-1,2,4-tricarboxylic acid-1,2-anhydride and 10 weight % of cyclohexane-1,2,4-tricarboxylic acid-1,2-anhydride-4-ethyl ester (having an average molecular weight of 201.0) obtained in Example 1 and 50 parts by weight of an alicyclic epoxy resin (Celoxide manufactured by DAICEL CHEMICAL INDUSTRIES, LTD., epoxy equivalent 126) were mixed (acid anhydride mol/epoxy equivalent ratio 0.9), whereby a heat-curable resin composition was obtained. The resin composition had a viscosity of 10.0 Pa·s at 30° C.

Table 7 shows the percentage by which the weight of the resultant resin composition reduces in each of the precuring and the postcuring, and the results of the evaluation of the cured product.

Example 9

73 parts by weight (0.36 mol) of an acid anhydride ester composition composed of 50 weight % of cyclohexane-1,2,4-tricarboxylic acid-1,2-anhydride and 50 weight % of cyclohexane-1,2,4-tricarboxylic acid-1,2-anhydride-4-ethyl ester (having an average molecular weight of 205.2) obtained in Example 2 and 50 parts by weight of an alicyclic epoxy resin (Celoxide manufactured by DAICEL CHEMICAL INDUSTRIES, LTD., epoxy equivalent 126) were mixed (acid anhydride mol/epoxy equivalent ratio 0.9), whereby a heat-curable resin composition was obtained. The resin composition had a viscosity of 1.5 Pa·s at 30° C.

Table 7 shows the percentage by which the weight of the resultant resin composition reduces in each of the precuring and the postcuring, and the results of the evaluation of the cured product.

Example 10

78 parts by weight (0.36 mol) of an acid anhydride ester composition composed of 50 weight % of cyclohexane-1,2,4-tricarboxylic acid-1,2-anhydride and 50 weight % of cyclohexane-1,2,4-tricarboxylic acid-1,2-anhydride-4-ethyl ester (having an average molecular weight of 219.2) obtained in Example 3 and 50 parts by weight of an alicyclic epoxy resin (Celoxide manufactured by DAICEL CHEMICAL INDUSTRIES, LTD., epoxy equivalent 126) were mixed (acid anhydride mol/epoxy equivalent ratio 0.9), whereby a heat-curable resin composition was obtained. The resin composition had a viscosity of 1.0 Pa·s at 30° C.

Table 7 shows the percentage by which the weight of the resultant resin composition reduces in each of the precuring and the postcuring, and the results of the evaluation of the cured product.

Comparative Example 1

60 parts by weight of methylhexahydrophthalic anhydride (RIKACID MH700 manufactured by New Japan Chemical Co., Ltd.), 0.13 part by weight of benzyldimethylamine as a curing accelerator, and 50 parts by weight of an alicyclic epoxy resin (Celoxide manufactured by DAICEL CHEMICAL INDUSTRIES, LTD., epoxy equivalent 126) were mixed. The resultant resin composition had a viscosity of 0.10 Pa·s at 30° C.

Table 7 shows the percentage by which the weight of the resultant resin composition reduces in each of the precuring and the postcuring, and the results of the evaluation of the cured product.

Comparative Example 2

35 parts by weight of cyclohexane-1,2,4-tricarboxylic acid-1,2-anhydride and 50 parts by weight of an alicyclic epoxy resin (Celoxide manufactured by DAICEL CHEMICAL INDUSTRIES, LTD., epoxy equivalent 126) were mixed. However, a good cured product free of any bubble was not obtained because the curing of the mixture progressed while bubbles were involved owing to a high curing rate.

Comparative Example 3

71 parts by weight (0.36 mol) of cyclohexane-1,2,4-tricarboxylic acid-1,2-anhydride (manufactured by MITSUBISHI GAS CHEMICAL COMPANY, INC.) and 50 parts by weight of an alicyclic epoxy resin (Celoxide manufactured by DAICEL CHEMICAL INDUSTRIES, LTD., epoxy equivalent 126) were mixed (acid anhydride/epoxy equivalent ratio 0.9), whereby a resin composition was obtained. The resin composition had a viscosity of 22.2 Pa·s at 30° C. The resin composition was flowed into a mold measuring 5 cm by 5 cm so as to have a thickness of 3 mm. However, a good cured product free of any bubble was not obtained because the curing of the mixture progressed while bubbles were involved owing to a high curing rate.

−40° C. to 100° C. is repeated 100 times, so the heat-curable resin composition is found to have extremely excellent thermal shock resistance.

What is claimed is:

1. An acid anhydride ester composition, comprising:
   (A) an acid anhydride ester which is a mono-ester and is represented by the following general formula (I):

TABLE 7

| | Example 4 | Example 5 | Example 6 | Example 7 | Example 8 | Example 9 | Example 10 | Comparative Example 1 |
|---|---|---|---|---|---|---|---|---|
| Acid anhydride ester | | | | | | | | |
| Substituent (R) | Ethyl | Methyl | 1-propyl | Ethyl | Ethyl | Methyl | 1-propyl | |
| Viscosity (25° C., Pa·s) | 0.65 | 1.42 | 0.47 | 0.65 | 0.65 | 1.42 | 0.47 | |
| Heat-curable resin composition | | | | | | | | |
| Composition (part(s) by weight) | | | | | | | | |
| (A) Acid anhydride ester | 81 | 76 | 86 | 38(50) | 7(10) | 38(50) | 38(50) | |
| (B) Acid anhydride | | | | 38(50) | 65(90) | 38(50) | 38(50) | |
| Epoxy resin | 50 | 50 | 50 | 50 | 50 | 50 | 50 | 50 |
| Methylhexahydrophthalic anhydride | | | | | | | | 60 |
| (Curing accelerator) | | | | | | | | |
| Benzyldimethylamine | | 0.13 | 0.13 | | | | | |
| 2-ethyl-4-methylimidazole | | | | | | | | 0.13 |
| Viscosity (30° C., Pa·s) | 0.28 | 0.42 | 0.30 | 1.3 | 10.0 | 1.5 | 1.0 | 0.10 |
| Results of evaluation of cured product | | | | | | | | |
| (1) Transmittance for light beam having wavelength of 400 nm (%/mm) | | | | | | | | |
| Initial stage | 85 | 87 | 88 | 90 | 89 | 90 | 88 | 84 |
| After UV resistance test (120 hr) | 83 | 78 | 83 | 78 | 87 | 79 | 83 | 81 |
| After heat resistance test (150° C., 120 hr) | 65 | 74 | 64 | 80 | 80 | 79 | 68 | 57 |
| (2) Thermal shock resistance test | x | x | x | ○ | ○ | ○ | ○ | x |
| (3) Percentage by which weight reduces (weight %) | | | | | | | | |
| Precuring (120° C., 3 hr) | 1 | 1 | 1 | 1 | 1 | 1 | 1 | 10 |
| Postcuring (150° C., 2 hr) | 0 | 0 | 0 | 0 | 0 | 0 | 0 | 1 |

As is apparent from Table 7, the acid anhydride ester of the present invention, and the heat-curable resin composition of the present invention composed of the acid anhydride ester and a compound having an epoxy ring each have a low viscosity, so the acid anhydride ester and the compound can be favorably blended with each other.

In addition, the following is found: the cured product of the heat-curable resin composition of the present invention is excellent in light beam permeability, shows no evaporation loss after curing even when the cured product is treated with heat or irradiated with UV, and can maintain a colorless and transparent nature. In addition, the following is found: the percentage by which the weight of the composition reduces at the time of each of precuring and postcuring is small, so a molded article having high accuracy can be obtained, and can be advantageously used in, for example, an encapsulant for a photoelectric conversion element.

Further, the heat-curable resin composition of the present invention composed of: the acid anhydride ester composition composed of (A) the acid anhydride ester and (B) cyclohexane-1,2,4-tricarboxylic acid-1,2-anhydride; and a compound having an epoxy ring (any one of Examples 7 to 10) is capable of not only showing the above properties but also curing without the use of any curing accelerator, and does not cause the generation of a crack even in a heat cycle in which a cooling and heating operation in the temperature range of

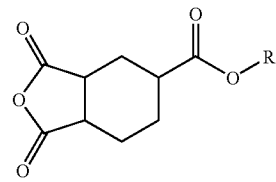

where R represents an alkyl group having 1 to 4 carbon atoms; and
   (B) cyclohexane-1,2,4-tricarboxylic acid-1,2-anhydride.

2. An acid anhydride ester composition according to claim 1, wherein a weight ratio (A):(B) is 95 to 5:5 to 95.

3. An acid anhydride ester composition according to claim 2, wherein a weight ratio (A):(B) is 60 to 10:40 to 90.

4. A curing agent, comprising the acid anhydride ester composition according to claim 1.

5. A heat-curable resin composition, comprising:
   the acid anhydride ester composition according to claim 1; and
   a compound having an epoxy ring.

6. A cured product obtained by curing the heat-curable resin composition according to claim 5.

* * * * *